(12) United States Patent
Miethke

(10) Patent No.: US 8,870,809 B2
(45) Date of Patent: Oct. 28, 2014

(54) IMPLANTABLE HYDROCEPHALUS SHUNT SYSTEM

(75) Inventor: Christoph Miethke, Potsdam (DE)

(73) Assignee: Christoph Miethke GmbH & Co KG, Potsdam (DE)

( * ) Notice: Subject to any disclaimer, the term of this patent is extended or adjusted under 35 U.S.C. 154(b) by 0 days.

(21) Appl. No.: 13/478,157

(22) Filed: May 23, 2012

(65) Prior Publication Data

US 2012/0232462 A1    Sep. 13, 2012

Related U.S. Application Data

(63) Continuation-in-part of application No. PCT/EP2010/007817, filed on Dec. 21, 2010.

(30) Foreign Application Priority Data

Dec. 23, 2009  (DE) .................. 10 2009 060 533

(51) Int. Cl.
| | |
|---|---|
| *A61M 5/00* | (2006.01) |
| *A61M 39/02* | (2006.01) |
| *A61M 27/00* | (2006.01) |
| *A61M 5/142* | (2006.01) |
| *A61M 1/36* | (2006.01) |
| *A61M 39/24* | (2006.01) |

(52) U.S. Cl.
CPC ......... *A61M 27/006* (2013.01); *A61M 39/0208* (2013.01); *A61M 2039/242* (2013.01); *A61M 5/14276* (2013.01); *A61M 2039/2473* (2013.01); *A61M 39/24* (2013.01); *A61M 1/3655* (2013.01)
USPC .............................................. 604/9

(58) Field of Classification Search
USPC ............................................... 604/9
See application file for complete search history.

(56) References Cited

U.S. PATENT DOCUMENTS

| | | | |
|---|---|---|---|
| 3,768,508 A | 10/1973 | Schulte | |
| 3,769,982 A | 11/1973 | Schulte | |
| 3,889,687 A * | 6/1975 | Harris et al. | .............. 604/10 |
| 4,443,214 A * | 4/1984 | Marion | .............. 604/9 |
| 4,552,553 A | 11/1985 | Schulte et al. | |
| 4,560,375 A | 12/1985 | Schulte et al. | |
| 4,676,772 A * | 6/1987 | Hooven | .............. 604/9 |

(Continued)

FOREIGN PATENT DOCUMENTS

| | | |
|---|---|---|
| DE | 102007059300 | 6/2009 |
| EP | 0646381 | 4/1995 |

(Continued)

*Primary Examiner* — Susan Su
*Assistant Examiner* — Guy K Townsend
(74) *Attorney, Agent, or Firm* — Nils H. Ljungman & Associates

(57) ABSTRACT

An implantable hydrocephalus shunt system. The abstract of the disclosure is submitted herewith as required by 37 C.F.R. §1.72(b). As stated in 37 C.F.R. §1.72(b): A brief abstract of the technical disclosure in the specification must commence on a separate sheet, preferably following the claims, under the heading "Abstract of the Disclosure." The purpose of the abstract is to enable the Patent and Trademark Office and the public generally to determine quickly from a cursory inspection the nature and gist of the technical disclosure. The abstract shall not be used for interpreting the scope of the claims. Therefore, any statements made relating to the abstract are not intended to limit the claims in any manner and should not be interpreted as limiting the claims in any manner.

20 Claims, 8 Drawing Sheets

(56) References Cited

U.S. PATENT DOCUMENTS

| | | | |
|---|---|---|---|
| 4,729,762 A * | 3/1988 | Doumenis | 604/10 |
| 4,885,002 A * | 12/1989 | Watanabe et al. | 604/9 |
| 4,904,236 A * | 2/1990 | Redmond et al. | 604/9 |
| 4,995,856 A * | 2/1991 | Heindl et al. | 604/8 |
| 5,069,663 A * | 12/1991 | Sussman | 604/9 |
| 5,154,693 A | 10/1992 | East et al. | |
| 5,167,615 A | 12/1992 | East et al. | |
| 5,368,556 A | 11/1994 | Lecuyer | |
| 5,468,221 A | 11/1995 | Schoener | |
| 5,575,770 A | 11/1996 | Melsky et al. | |
| 5,637,083 A | 6/1997 | Bertrand et al. | |
| 5,643,195 A | 7/1997 | Drevet et al. | |
| 5,662,600 A * | 9/1997 | Watson et al. | 604/8 |
| 5,728,061 A | 3/1998 | Ahmed | |
| 5,795,307 A | 8/1998 | Krueger | |
| 5,800,376 A * | 9/1998 | Watson et al. | 604/9 |
| 5,843,013 A | 12/1998 | Lecuyer et al. | |
| 5,928,182 A | 7/1999 | Kraus et al. | |
| 5,935,084 A | 8/1999 | Southworth | |
| 6,083,179 A | 7/2000 | Oredsson | |
| 6,090,062 A * | 7/2000 | Sood et al. | 604/9 |
| 6,126,628 A * | 10/2000 | Nissels | 604/9 |
| 6,193,682 B1 * | 2/2001 | Ahmed | 604/9 |
| 6,264,625 B1 * | 7/2001 | Rubenstein et al. | 604/9 |
| 6,383,159 B1 | 5/2002 | Saul et al. | |
| 6,391,019 B1 * | 5/2002 | Ito | 604/891.1 |
| 6,485,449 B2 * | 11/2002 | Ito | 604/9 |
| 6,575,928 B2 | 6/2003 | Saul et al. | |
| 6,805,687 B2 | 10/2004 | Dextradeur et al. | |
| 6,875,192 B1 | 4/2005 | Saul et al. | |
| 6,926,691 B2 * | 8/2005 | Miethke | 604/9 |
| 7,025,739 B2 | 4/2006 | Saul | |
| 7,118,548 B2 | 10/2006 | Borgesen | |
| 7,192,413 B2 | 3/2007 | Kraus et al. | |
| 7,422,566 B2 * | 9/2008 | Miethke | 604/9 |
| 7,513,883 B2 * | 4/2009 | Glenn | 604/8 |
| 7,559,912 B2 * | 7/2009 | McCusker et al. | 604/9 |
| 7,766,855 B2 * | 8/2010 | Miethke | 604/9 |
| 2001/0022350 A1 * | 9/2001 | Ito | 251/65 |
| 2002/0022793 A1 * | 2/2002 | Bertrand et al. | 604/9 |
| 2002/0026139 A1 | 2/2002 | Bertrand et al. | |
| 2002/0045847 A1 * | 4/2002 | Borgesen | 604/9 |
| 2002/0128588 A1 * | 9/2002 | Borgesen | 604/9 |
| 2003/0057392 A1 * | 3/2003 | Ito | 251/11 |
| 2003/0139699 A1 * | 7/2003 | Rosenberg | 604/9 |
| 2003/0163079 A1 * | 8/2003 | Burnett | 604/9 |
| 2004/0024346 A1 * | 2/2004 | Miethke | 604/9 |
| 2004/0030279 A1 | 2/2004 | Rubenstein et al. | |
| 2004/0082900 A1 * | 4/2004 | Luttich | 604/9 |
| 2004/0122348 A1 * | 6/2004 | Hokanson et al. | 604/9 |
| 2004/0193094 A1 * | 9/2004 | Kraus | 604/8 |
| 2004/0267187 A1 * | 12/2004 | Rosenberg | 604/9 |
| 2005/0038371 A1 | 2/2005 | Reich et al. | |
| 2005/0096579 A1 * | 5/2005 | Bertrand et al. | 604/9 |
| 2005/0096581 A1 * | 5/2005 | Chan | 604/9 |
| 2005/0096582 A1 * | 5/2005 | Burnett | 604/9 |
| 2005/0096633 A1 * | 5/2005 | Moskowitz | 604/508 |
| 2005/0245887 A1 * | 11/2005 | Olsen et al. | 604/284 |
| 2005/0273034 A1 * | 12/2005 | Burnett | 604/9 |
| 2006/0036208 A1 * | 2/2006 | Burnett | 604/9 |
| 2006/0074371 A1 * | 4/2006 | McCusker et al. | 604/9 |
| 2006/0089589 A1 * | 4/2006 | Portnoy | 604/9 |
| 2006/0138370 A1 * | 6/2006 | Biehl et al. | 251/11 |
| 2007/0004999 A1 * | 1/2007 | Miethke | 604/9 |
| 2007/0005000 A1 * | 1/2007 | Ludin | 604/9 |
| 2007/0032757 A1 * | 2/2007 | Medow et al. | 604/9 |
| 2007/0078398 A1 * | 4/2007 | Dextradeur et al. | 604/167.01 |
| 2007/0093741 A1 * | 4/2007 | Miethke | 604/9 |
| 2007/0112293 A1 * | 5/2007 | Borgesen | 604/9 |
| 2008/0097277 A1 * | 4/2008 | Saunders | 604/9 |
| 2008/0132823 A1 * | 6/2008 | Rosenberg | 604/9 |
| 2008/0154173 A1 * | 6/2008 | Burnett | 604/9 |
| 2008/0281250 A1 * | 11/2008 | Bergsneider et al. | 604/9 |
| 2009/0005720 A1 * | 1/2009 | Ludin et al. | 604/9 |
| 2009/0054827 A1 * | 2/2009 | Eide | 604/9 |
| 2009/0112103 A1 | 4/2009 | Kassem | |
| 2010/0030103 A1 * | 2/2010 | Lutze et al. | 600/561 |

FOREIGN PATENT DOCUMENTS

| | | |
|---|---|---|
| EP | 0 888 795 A1 | 1/1999 |
| EP | 1 462 144 A1 | 9/2004 |
| WO | WO 9832482 | 7/1998 |

* cited by examiner

IMPLANTABLE HYDROCEPHALUS SHUNT SYSTEM

This application is a Continuation-In-Part application of International Patent Application No. PCT/EP2010/007817, filed on Dec. 21, 2010, which claims priority from Federal Republic of Germany Patent Application No. 10 2009 060 533.9, filed on Dec. 23, 2009. International Patent Application No. PCT/EP2010/007817 was pending as of the filing date of this application. The United States was an elected state in International Patent Application No. PCT/EP2010/007817.

BACKGROUND

1. Technical Field

The present application relates to a subcutaneously implantable hydrocephalus shunt system.

2. Background Information

Background information is for informational purposes only and does not necessarily admit that subsequently mentioned information and publications are prior art.

In medicine, a connection between normally separated vessels or cavities is called a shunt. Various synthetic shunts are known. Malformations that occur in nature and likewise make a connection between vessels or cavities are not considered in the following use of the term shunt.

Shunts between the arterial and venous circulatory system may be important. This type of shunt may serve to improve the oxygen supply of the patient.

With dialysis patients, a shunt is implanted in order to develop a high volume vessel for hemodialysis.

A shunt may be provided between the *Areteria radians* and the *Vena cephalica* on the forearm.

For patients with kidney damage, dialysis shunts may be essential for survival.

In neurosurgery with hydrocephalus cases, the shunt may be of major importance for draining off the liquor. This is mostly a tube or passage led subcutaneously from the cranium down through the throat into the upper *vena cava* or from the thoracic wall to the abdominal cavity.

There are also various other shunts of lesser importance.

Shunts provided for hydrocephalus may be provided with a valve in order to control or regulate the discharge of the liquor in the shunt. More recently, adjustable valves may be used. The drain liquid is then the liquor.

Various ailments of the patients can be alleviated not only by liquid discharge, but also through treatment with medicaments/pharmaceuticals, and possibly eliminated and/or reduced and/or minimized. The technical problem of the present application was to administer to the patient these medicaments/pharmaceuticals in liquid form or with the aid of liquids.

OBJECT OR OBJECTS

The present application emanates from the consideration of delivering the medicaments/pharmaceuticals as a liquid or with the aid of a liquid through the drainage tube or passage to the site of the disease. The liquid flow according to the present application is intended to temporarily interrupt and overcome the drainage flow, such that a flow occurs in the opposite direction. Surprisingly, an interruption over short periods of time is harmless.

SUMMARY

One possible addition of medicaments/pharmaceuticals in liquid form or with the aid of liquids may be achieved by means of a bidirectional valve design. A liquid flow of this type can also optionally be achieved with the aid of a parallel switch/parallel system of closures, of which the one closure opens in the drainage direction and the second closure arranged/switched in parallel opens with a higher liquid pressure in the direction according to the concept in the present application.

In at least one possible embodiment, the present application can also be used for the addition of contrast agents or other liquids that are conducive for treating/examining patients.

Use of the present application makes possible the administration of treatment liquids in the opposite direction to any drainage direction of bodily fluid. This means, for example that a liquid addition is possible in the proximal direction with a simultaneous and/or substantially simultaneous closure of the distal outlet. Or an administration of liquids is possible in the distal direction with a simultaneous and/or substantially simultaneous closure of the proximal outlet. The same applies for other directions.

The present application works optionally independently or dependently of the body position of the patient.

The valve according to at least one possible embodiment of the present application may possess a housing with inlet and outlet and at least one interior chamber for the drainage liquid which is connected to the inlet and the outlet.

At least one additional interior chamber can also be optionally provided, out of which a liquid flow according to the present application can be caused. This additional chamber is at least connected to the inlet of the valve in order to produce a liquid flow directed opposite to the drainage flow.

At least one additional interior chamber can also be optionally provided, in which the treatment liquid and drainage liquid are mixed.

This can be intended when the concentration of the treatment agent should be decreased.

In contrast, when a highest possible concentration of the treatment agent is aimed for, then an interior chamber may possibly be utilized, in which treatment liquid alone is stored.

In the valve housing there is a closing part/closure that in one possible embodiment of the present application conventionally formed by a valve cap/valve plate or by a ball valve. This applies for example for closures that are arranged/switched in parallel.

In at least one possible embodiment of the present application, the draining operation is differentiated from the liquid dosing in the valve.

The draining operation can occur in the same way as in other valves:

In the draining operation the drain liquid has to and/or may overcome the resistance of the closing part/closure in the valve in order to be able to flow through the valve. In at least one possible embodiment of the present application, the resistance results from a spring tension. Valves with ball valves are also known, whose sole weight or together with other parts, in one possible embodiment with a spring, creates the resistance. In conventional valves the resistance of the closing part/closure prevents and/or restricts and/or minimizes any unwanted excess drainage, i.e. an unwanted discharge of too much drainage liquid. Contemporary valves, moreover, are adjustable in order to match the drainage to the respective patient and to the illness.

The contemporary valves also act as non-return valves. A return flow of drainage liquid is prevented, restricted, and/or minimized. In practical terms, a return flow of drainage liquid occurs with low pressure. In at least one possible embodiment, the present application utilizes valves that are intended to show both a drain function as well as a liquid flow against the direction of the drainage flow.

The present application compensates for the non-return function in this variant by using a higher pressure than that which is present for a reflux of drainage liquid. The present application thereby forces the valve into an open position for a temporary ingress of the drainage tube or passage with liquids, in which medicaments or pharmaceuticals are present or which comprise these or of similar substances. Some similar substances also include contrast agents or liquids comprising contrast agents or also rinse liquid. In at least one possible embodiment of the present application, the ingress forces a liquid flow against the drainage direction in the drainage tube or passage.

According to the present application, a switch causes the valve to open, thereby admitting the liquid in the direction opposed to the drainage direction. The switch is integrated in the valve housing and is in one possible embodiment formed by a mechanical and/or hydraulic means. The external liquid or drainage liquid or the liquid provided for the medicament/pharmaceutical or similar substance is optionally used for the hydraulic actuation.

Depending on the use of the liquid, different switches may be used, utilized, and/or adapted for use.

In at least one possible embodiment of the present application, valves may be used, in which the liquid to be administered opens the valve part and flows through the valve against the drainage direction.

In at least one possible embodiment of the present application, a special valve cap/valve plate may be used that, as discussed above, is held both with clearance in a guide between the valve seat and with a spring. The clearance provides a limited freedom of movement to the valve cap/valve plate. As a result of the movement, the drainage liquid can flow with ease past the valve cap/valve plate into the valve. At the same time the guide ensures or essentially ensures, in the case of a reflux of the drainage liquid, that the valve cap/valve plate seals the inlet of the valve. Here, the reflux presses the valve cap/valve plate against the valve seat.

In at least one possible embodiment of the present application, the guide for the valve cap/valve plate may be formed by the valve seat on one side and by a spring on the other side. In the closed position of the valve (valve cap/valve plate is on the valve seat) the spring is disposed at a distance corresponding to the desired clearance of the valve cap.

Optionally there is also a guide ring that guides and surrounds the valve cap/valve plate. The guide ring can be matched to any contour of the valve cap/valve plate. This also applies to a valve cap/valve plate with a rectangular outline in the top view. Valve caps/valve plates of this type may be suitable for being opened with a tilting movement.

In the context of the drainage operation, the valve cap/valve plate on being opened initially builds up a resistance when the valve cap/valve plate is pressed against the spring by the drainage liquid.

In this regard, provision can be made that the valve cap/valve plate has already reached the maximum opening position when it abuts against the spring. An additional opening movement against the spring resistance can also be optionally provided.

In another variant of the valve in the closed position, the spring optionally lays against the valve cap/valve plate in a pressureless manner. The opening movement then immediately and/or substantially immediately builds up a resistance against the opening.

In a third variant the spring can also lay against the valve cap/valve plate in a pressurized manner. The valve cap/valve plate is then pressed into the closed position by a spring. The spring pressure is designed such that under conditions of normal drainage the valve cap/valve plate opens due to the pressure of the flowing drainage liquid or opens once the spring has been pressed together.

The specified and/or desired deformation path of the spring and its design determine the resistance against opening.

The spring can be moved mechanically or hydraulically to change (increase/decrease) the resistance.

To open the drainage tube or passage to let in the liquid to be administered (hereinafter called medicament liquid), the valve cap/valve plate is opened against the pressure of the medicament liquid and/or against mechanical pressure.

This is achieved by a flexible membrane or a plunger and a lever bar that is located between the membrane and the valve cap/valve plate.

The medicament liquid puts pressure on the membrane or the plunger. This is harmless if the medicament liquid simultaneously and/or substantially simultaneously presses on the valve cap/valve plate. In fact in this way the resistance against an opening movement of the valve cap/valve plate is correspondingly increased.

In at least one possible embodiment, the valve cap/valve plate opens when: (A) the membrane surface or plunger surface is pressurized to a suitably greater degree by the medicament liquid than is the surface of the valve cap/valve plate, and the membrane or the plunger acts with sufficient force on the lever bar; and/or (B) when a pressure is additionally exerted manually or with a drive on the implanted valve.

When medicament liquid impacts the membrane or the plunger, various situations can be considered.

In one variant of the present application, the membrane is impacted in its direction of actuation or the plunger is impacted in its direction of actuation with medicament liquid. The actuation pressure then depends on the specific and/or desired pressure of the medicament liquid and on the surface of the membrane or plunger impacted by the liquid.

In another variant of the present application, the medicament liquid differs from the first variant in that it also reaches the opposite surface of the membrane or plunger. Then the pressure there where the surface is impinged with liquid partially offsets the actuating pressure. Then the resulting pressure depends on the differential pressure. The actuating pressure is the pressure at which the valve cap or the valve plate is opened against the medicament liquid flowing in the direction of closure.

In this regard, when the medicament liquid acts at the same time in the flow direction on the valve cap or valve plate, then this likewise acts against the opening, and the actuating pressure must and/or should also overcome this.

In at least one possible embodiment of the present application, in order to ensure and/or substantially ensure the actuation of the valve cap or the valve plate, there is provided according to the present application that the membrane surface or plunger surface impinged with medicament liquid in the direction of actuation is in one possible embodiment somewhat larger than the sum of the membrane surface or plunger surface impinged in the opposite direction (opposite the direction of actuation) plus the valve cap surface or valve plate surface impinged by the medicament liquid in the direction of closure.

The membrane surface or plunger surface impinged with medicament liquid is in at least one possible embodiment at least twenty percent, even more in one possible embodiment at least forty percent and in one possible embodiment sixty percent greater than the previously mentioned surfaces.

The surface relations and pressure conditions can optionally be modified during the actuation movement of the membrane or the plunger.

In at least one possible embodiment, openings are provided in the membrane or plunger for the passage of the drainage liquid and/or the medicament liquid. When the membrane or the plunger is impacted in the direction of actuation with medicament liquid, then the medicament liquid flows through the openings. Depending on the widths of the openings and the number of openings and depending on the pressure and empty space behind the membrane or the plunger, there results a certain time until an appreciable obstructive pressure for the actuation step is built up in this empty space. At the same time it should also be noted that the membrane or the plunger needs and/or desires a certain time to actuate the lever bar and open the valve cap/valve plate. By adjusting the opening width, in at least one possible embodiment of the present application by closing some openings (varying the number of the open openings), optionally by modifying the volume of the hollow space and/or the pressure, one can ensure and/or substantially ensure that the actuation movement terminates before an appreciable pressure is built up in the hollow space. Here, the opening path of the valve cap/valve plate has a favorable effect, because with the initial opening of the valve cap/valve plate, the medicament liquid can escape into the drainage tube or passage against its direction of drainage. This can completely or partially prevent and/or restrict and/or minimize an obstructive pressure of the valve cap/valve plate opening building up against the direction of actuation on the membrane surfaces or on the plunger surfaces.

In at least one possible embodiment of the present application, after the valve cap/valve plate opens, the membrane or the plunger assumes an end position, in which a sufficient differential surface is ensured and/or substantially ensured. In this regard the membrane or the plunger lies with the surface, on which a pressure directed against the direction of actuation can build up, wholly or partially on a housing surface.

In the following, when a pressure impacted surface on the membrane or on the plunger is mentioned, then this includes the previously mentioned differential surface.

In at least one possible embodiment of the present application, the specific and/or desired medicament liquid for pressurizing the membrane or the plunger is pressed out of a housing chamber of the valve. This can be achieved by manually deforming the chamber wall.

For the deformation, the chamber is designed to be flexible, at least partially, namely on the area to be deformed.

Such reservoirs are provided in the known applications for collecting drainage liquid (liquor). This reservoir is designed to rinse free the drainage tube or passage and the valve in the case of a recognizable blockage of the drainage tube or passage or of the valve.

The blockage is easily caused by pieces of tissue or blood clots, which accumulate in the tube or passage or in valve parts. This can cause the drainage in the tube or passage to be interrupted and in the valve can block the valve in the open position. The interruption prevents, restricts, and/or minimizes a required and/or desired drainage. A lasting open position causes a similarly harmful over-drainage.

Some reservoirs may mostly comprise flexible silicone.

Some reservoirs are actuated manually, i.e. pressed together.

Some of the reservoirs have a curved shape. They are actuated by pressing on the curvature.

According to the present application, a housing is provided for the device of the present application and possesses a curved flexible side on the side opposite to the closure. The housing forms a reservoir there. This reservoir can be filled with medicament liquid. The medicament liquid can be squeezed out of the reservoir by pressing on the curved side of the housing.

The resulting pressure is high enough to open the described closure on the valve inlet, such that a flow of medicament liquid can exit from the valve against the direction of drainage.

Silicone walls may be pierced with a syringe without problem.

This allows the reservoir to be filled with medicament liquid with the aid of a syringe even once the valve has been implanted. Once the reservoir in the housing has been filled the syringe can be removed without problem and the silicone self-sealingly closes the injection point. Such housing walls are also called a port. Some materials for pierceable walls are silicone or rubber or comparable elastomers.

The medicament liquid can be held in a specific reservoir in the housing, such that a plurality of medicament administrations are possible with one reservoir filling.

In at least one possible embodiment of however, the housing is filled with the medicament liquid for each medicament administration and promptly utilized.

The medicament liquid is optionally filled up in pure form or in a mixture with another biocompatible liquid in order to carry out the above described medicament administration.

The drainage liquid is also optionally utilized for admixing with the medicament liquid. In this regard the reservoir, just as for some reservoirs, can be utilized to collect drainage liquid and the medicament liquid can be injected after partial or complete filling of the reservoir. With a completely filled reservoir, the injection of medicament liquid leads to an immediate and/or substantially immediate drainage of the excess amount of liquid. Incidentally, the medicament liquid is mixed with the drainage liquid.

In one possible embodiment of the present application, the use of a known reservoir for the valve of the present application is the possibility for alternative operation of the valve of the present application for a conventional drainage including conventional rinsing exclusively with drainage liquid between two medicament administrations.

A further possibility includes, instead of the medicament liquid alone or in a mixture with drainage liquid, dispatching a rinse liquid into the reservoir of the valve of one possible embodiment of the present application.

One can also consider a plurality of cavities in the housing that form reservoirs, in which medicament liquid can be held separate from other liquids.

According to the present application, damage to the syringe and valve are avoided and/or minimized when using a syringe to fill the valve.

On the actuation side, the membrane or the plunger is optionally provided with a funnel-shaped indentation. This guides the syringe needle away from the edge to the center. During the filling operation this prevents, restricts, and/or minimizes the needle from slipping towards the edge and being trapped in the openings that are located there through which the medicament liquid and/or the drainage liquid flows.

Alternatively or additionally, the membrane or the plunger on the contact surface with the syringe needle is designed to be slip resistant and/or non-slip. For this the surface can be suitably profiled or coated, in one possible embodiment with a puncture-proof plastic. A lattice structure can also prevent, restrict, and/or minimize any slipping.

The volume of the syringe is matched to the required and/or desired quantity of medicament liquid for one filling operation. The quantity comprises:
 a) the quantity of liquid that should exit from the drainage tube or passage;
 b) the quantity of liquid that is required and/or desired for filling the drainage tube or passage from the valve up to the outlet end on the drainage tube or passage;
 c) the quantity of liquid that is required and/or desired for filling the cavity in the valve housing.

Once the syringe has been emptied the above quantity a) is in the intended place. The pressure in the valve housing drops. The valve cap/valve plate, due to its spring loading, again takes up the intended position and the drainage operation continues. This involves
 a) initially the medicament liquid comprised in the valve housing and in the drainage tube or passage is discharged before the drainage fluid is discharged; or
 b) the medicament liquid comprised in the valve housing and in the drainage tube or passage is discharged together with drainage liquid;
 c) the membrane or the plunger moves back into the starting position.

The present application may also be applied to valves that are conventionally equipped with valve balls. Balls of this type are usually similarly spring loaded. A lever bar can also be used on the balls as in the valve cap/valve plate. Whereas for the valve cap/valve plate a simple angled lever that is connected on one side with the cap can be sufficient, on whose other end the membrane or the plunger presses, a fork that encloses the ball is optionally provided for a valve ball. The fork forms the one lever end. The lever is hinged between the fork end and the other lever end.

The membrane or plunger can then press again onto the other end.

The above-discussed embodiments of the present invention will be described further herein below. When the word "invention" or "embodiment of the invention" is used in this specification, the word "invention" or "embodiment of the invention" includes "inventions" or "embodiments of the invention", that is the plural of "invention" or "embodiment of the invention". By stating "invention" or "embodiment of the invention", the Applicant does not in any way admit that the present application does not include more than one patentably and non-obviously distinct invention, and maintains that this application may include more than one patentably and non-obviously distinct invention. The Applicant hereby asserts that the disclosure of this application may include more than one invention, and, in the event that there is more than one invention, that these inventions may be patentable and non-obvious one with respect to the other.

BRIEF DESCRIPTION OF THE DRAWINGS

At least one possible embodiment of the present application is explained in greater detail below with reference to the accompanying drawings.

DESCRIPTION OF EMBODIMENT OR EMBODIMENTS

Figure 1:
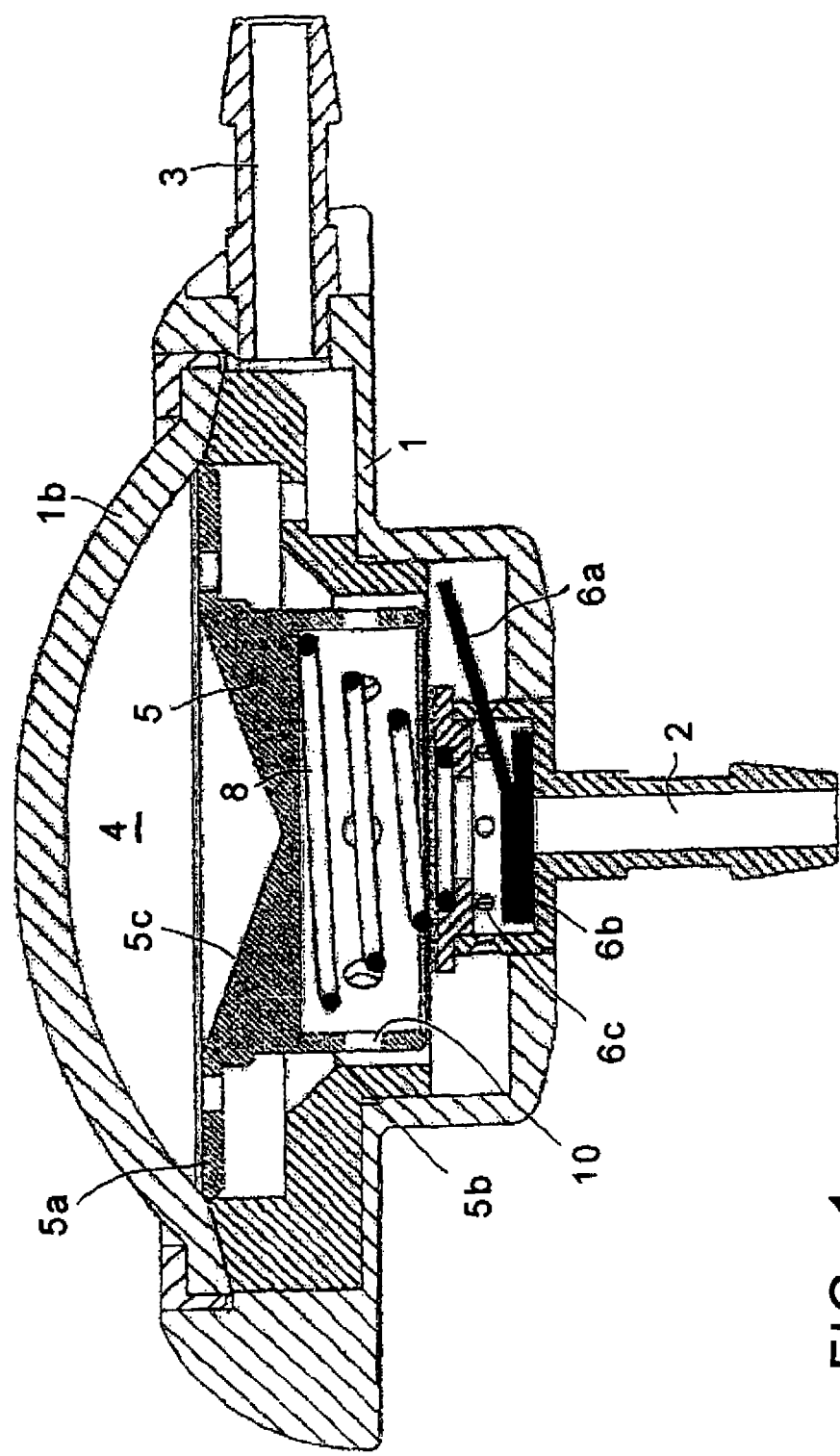
FIG. 1 shows an implanted hydrocephalus valve in at least one operational state.
Figure 2:
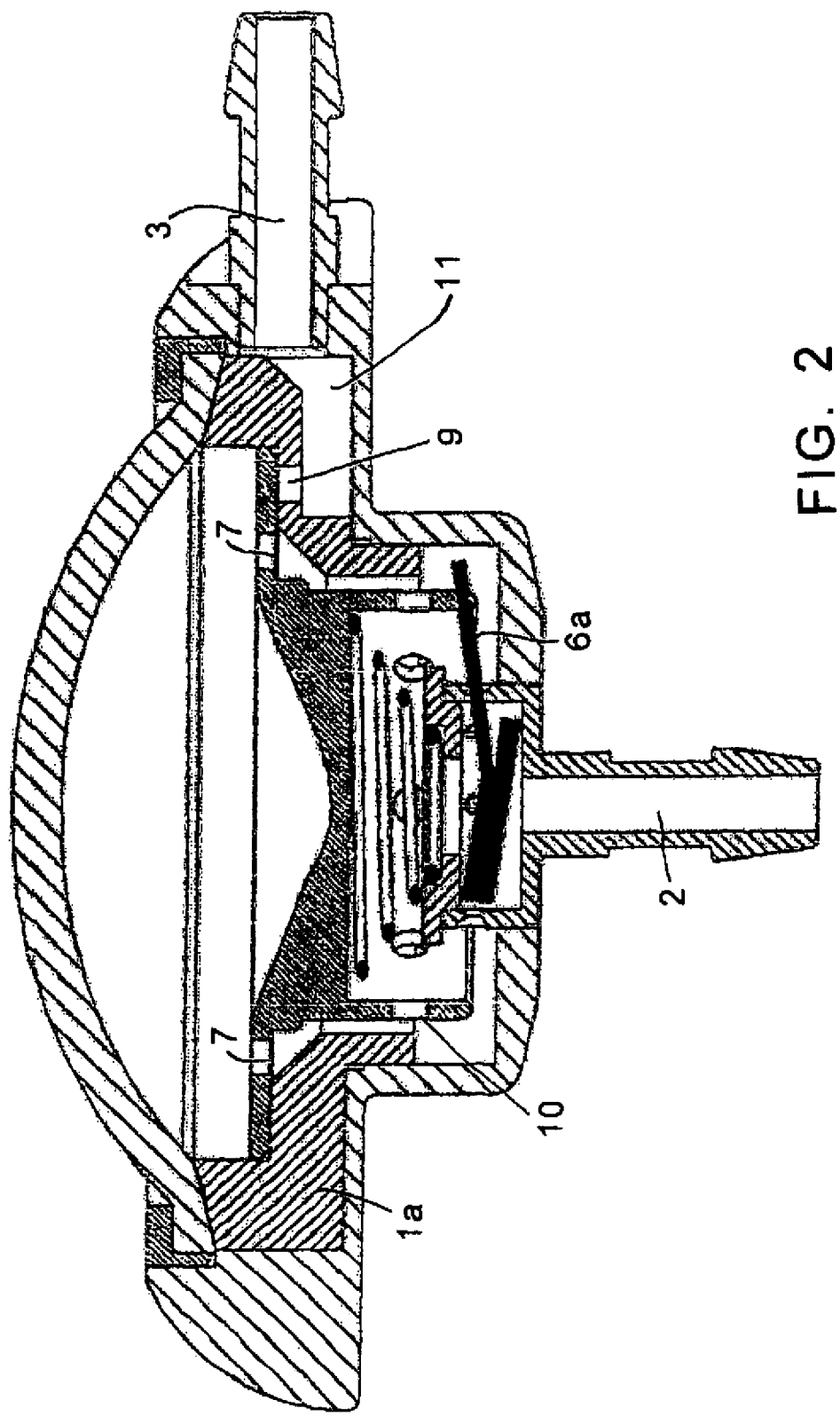
FIG. 2 shows an implanted hydrocephalus valve in at least one operational state.

FIGS. 1 and 2 show the implanted hydrocephalus valve in various operational states. The valve is a component of a liquor drainage. Here an implanted drainage tube or passage leads from a ventricle catheter to the valve and a further implanted drainage tube or passage from the valve in the stomach of the patient.

The valve comprises a housing 1 with an inlet 2, an outlet 3, an interior and cavity 4. A valve cap 6b that seals the inlet 2 with a lever 6a is provided in the interior of the valve. The valve cap 6b is let in the housing such that the valve cap in the embodiment does not need and/or desire a hinged connection with the housing. The valve cap 6b corresponds to a lid that however, because of the guiding in the housing and because of the collaboration of lever 6a with the plunger 5, behaves as a valve cap and is therefore designated here as a valve cap.

In other embodiments, another guiding or a hinged connection with the housing is provided instead of the guiding in the housing. Hinges of this type are conventionally comprise a hinge pin. Furthermore, the hinges have a plurality of hinge parts, of which the one parts are fixed on the housing or are formed by the housing and of which the other parts are fixed on the valve cap or are formed by the valve cap, wherein all and/or substantially all and/or some hinge parts are traversed by the hinge pin and are rotatable around the hinge pin.

Further, a plunger 5 is displaceably held in a lower cylindrical part of the housing 1. The plunger 5 is located with a lower, hollow shaped part 5b in the cylindrical part of the housing 1. Moreover, the plunger 5 with an edge 5a is displaceably located in an upper cylindrical part of the housing 1.

The lower cylindrical part and the upper cylindrical part of the housing are formed by a housing insert. At the same time the housing insert is shaped such that there results a guide tube or passage to the outlet 3 in the housing.

In the cavity there is a spiral spring 8 that in the embodiment is at a distance from the valve seat that is greater than the thickness of the valve cap. The bearing area of the valve cap on the inlet side is called the valve seat.

In another embodiment, the spiral spring presses on the valve cap.

In the illustrated embodiment, as a result of the described gap and the thus associated clearance, the valve cap can be freely moved to a limited extent between the valve seat and the spring. Moreover, when the opening force of the valve cap is high enough, the valve cap, once laid onto the spiral spring, can move further against its resistance. Once pressed together in this way the spring 8 is stretched again, when the opening force of the valve cap decreases, or the spring 8 immediately and/or substantially immediately reverts back into the described starting position when no more opening force is exerted on the valve cap.

At the same time, the spiral spring 8 on the valve cap side together with the valve cap 6b is centered in a housing ring and is nonetheless movable.

At the opposite end the spring 8 is guided in the plunger 5. Moreover, the housing ring possesses flow openings 6c.

In the operational state of the valve for the drainage, liquor penetrates into the outlet 2, from there through the opened valve cap 6b into the interior of the valve. The liquor flows from the open valve cap 6b through openings 10 that are uniformly distributed on the periphery of the plunger 5 into a gap between plunger 5 and housing 1. The gap leads to a plurality of uniformly distributed openings 9 in the rim 5a of the plunger 5.

The gap leads into a circular part of the interior in the operational state which is connected through an opening 9 to the tube or passage 11. The liquor can be discharged from the tube or passage 11 through the outlet 3.

FIG. 1 shows the operational state for a decreasing amount of liquor. The valve cap is then closed. This state differs from the previously described drainage state in the position of the valve cap.

FIG. 2 shows the operational state of the valve during injection (not shown) of medicament liquid with a syringe into the cavity above the plunger 5. The syringe is prevented, restricted, and/or minimized from slipping onto the rim 5a by a funnel shaped contact surface 5c of the plunger.

Injection of the medicament liquid is possible because the housing wall 1b to be penetrated is made of silicone.

Under the pressure of the medicament liquid and that of the syringe tip exerted on the plunger, the plunger 5 is moved into the position illustrated in FIG. 2. Here the opening 11 for the outlet 3 has been closed and the valve cap 6b opened.

At the same time, the medicament liquid is given the opportunity to flow through openings 7 in the rim 5a into the cited gap and through the openings 10 into the outlet and through the drainage tube or passage to the ventricle catheter. From there the medicament liquid can exit.

After emptying the syringe, the discharge of additional medicament liquid from the cavity of the housing leads to a drop in pressure there. Within a short time the abovementioned drainage operation recommences. The described liquor discharge occurs at a minimal liquor pressure. The drainage amount is low at a minimal liquor pressure. As described above, the liquor pressure can also be greater than the spring pressure, resulting in a greater opening of the valve. Such liquor pressures result in a significantly higher drainage amount. As long as the spring pressure is stronger than the liquor pressure, the spring pressure ensures and/or substantially ensures or promotes that the valve cap may be moved in the limit of the above described clearance. As the drainage operation recommences, the remaining medicament liquid in the valve and in the drainage tubes or passages is likewise discharged.

Figure 1A:
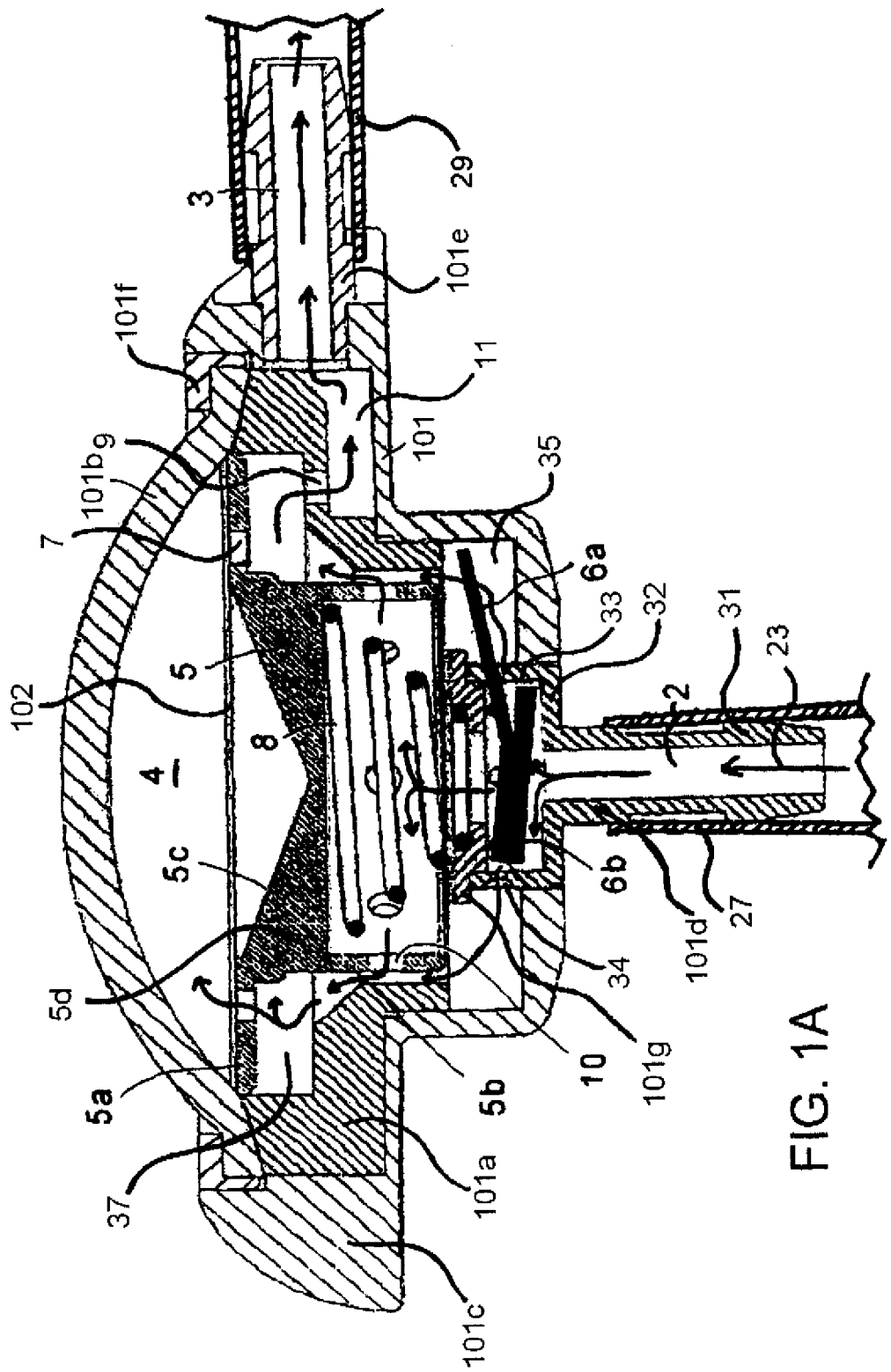
FIG. 1A shows a view of a hydrocephalus valve according to at least one possible embodiment of the present application.

FIG. 1A shows a view of a hydrocephalus valve according to at least one possible embodiment of the present application. It should be understood that the embodiment shown in FIG. 1A is one possible embodiment, and other variations and configurations of this embodiment are well within the scope of this application. Some of the reference numerals for corresponding parts or components in other figures have been utilized in this figure. In the embodiment shown, the hydrocephalus valve has a housing 101 which is comprised of at least the following components: a substantially cylindrical portion 101a, a wall 101b, an outer body portion 101c, an inlet portion 101d, an outlet portion 101e, a wall-retaining portion 101f, and a support disc 101g. The cylindrical portion 101a acts as a guide/housing for the plunger 5, specifically guiding the outer edge of the projecting ring portion 5a of the plunger 5 during the movement of the plunger 5. The cylindrical portion 101a is supported and/or held within a large cavity 4 formed by the outer body portion 101c. This cavity 4 is enclosed by the wall 101b, which has an inner edge, junction, or shoulder 102. The cavity 4, in the embodiment shown, is divided into sub-cavities or sub-chambers, specifically annular space 37 and opening or space 11. The inlet portion 101d is formed from a substantially tubular portion 31, a shoulder portion 32, and a ring-shaped or annular portion 33, which contains openings 34. The valve cap 6b is disposed within the ring-shaped portion 33. The inlet portion 101d is partially inserted into an opening in the outer body portion 101c. The outlet portion 101e is composed of a substantially tubular portion and is inserted into another opening in the outer body portion 101c. The support disc 101g acts as a support against which the spring 8 can be compressed by the movement of the plunger 5. The support disc 101g has a shoulder which engages an end of the annular portion 34 of the inlet portion 101d.

Figure 2A:
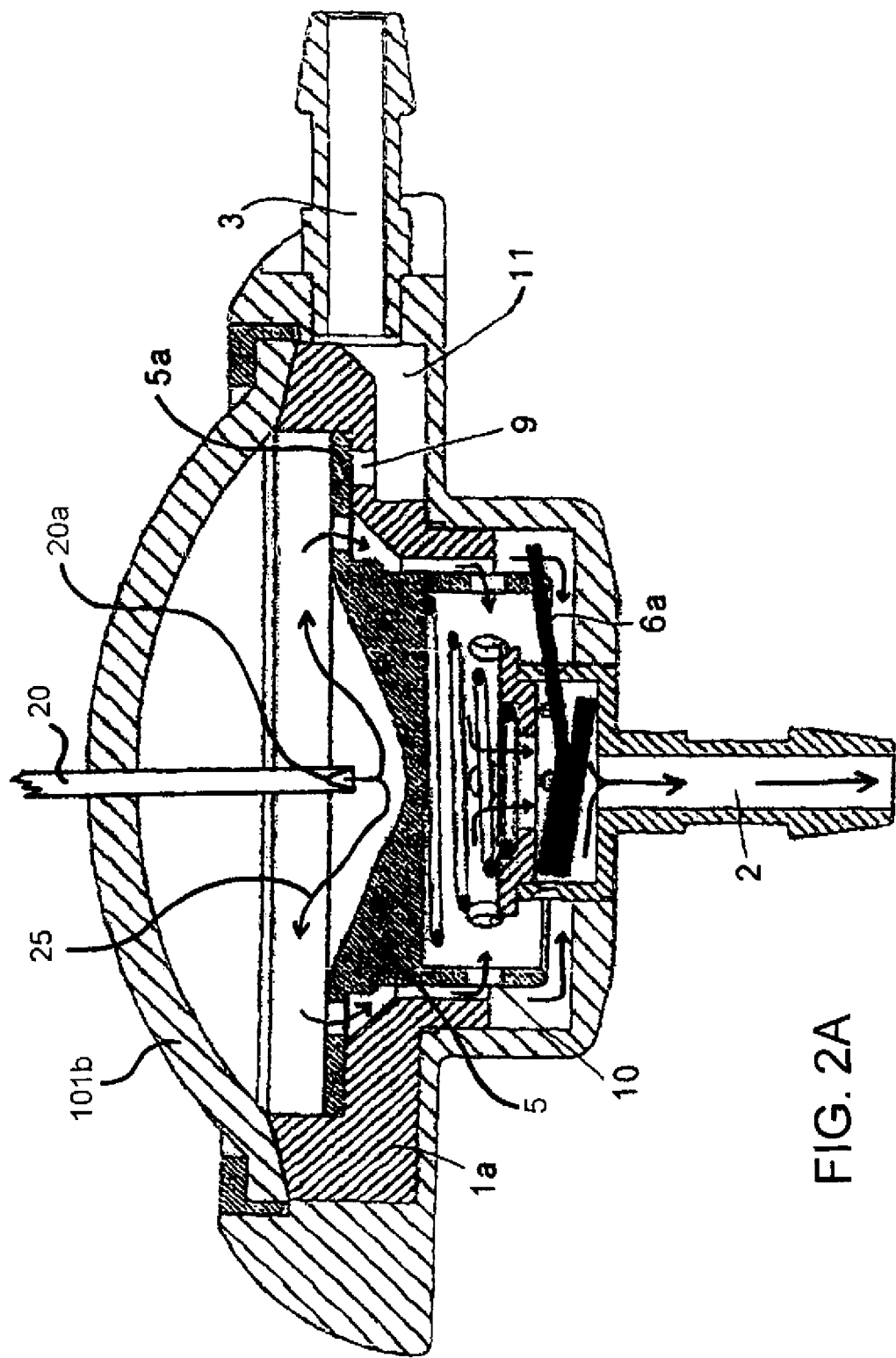
FIG. 2A shows a view of a hydrocephalus valve according to at least one possible embodiment of the present application.

In operation, drainage liquid, which may be liquor or cerebrospinal fluid (CSF), flows into the inlet 2. The flow path 23 of drainage fluid is shown by a number of arrows. When the pressure of the incoming drainage liquid on the inlet side of the valve cap 6b is greater than the pressure on the other side of the valve cap 6b, the valve cap 6b is displaced from the position shown in FIG. 1 in which the valve cap 6b is resting against the shoulder portion 32. FIG. 1A shows an example of the valve cap 6b in a possible position as a result of displacement. Drainage fluid flows past and/or around the valve cap 6b and out through the openings 33 into the cavity 35 surrounding the ring-shaped portion 33, and then into the space between the housing portion 101a and the hollow shaped part 5b. Drainage fluid also flows substantially centrally past the spring 8 and into the interior of the hollow shaped part 5b, before flowing out through the openings 10. The drainage fluid then flows into the cavity 37 disposed about a portion of the plunger 5. Openings 7 connect the cavity 4 with the annular cavity 37, so it is possible for some drainage fluid to flow into the cavity 4. When the plunger 5 is depressed, as shown in FIG. 2A, for example, the annular cavity 37 is essentially merged with the cavity 4. After the drainage fluid flows into the cavity 37, the drainage fluid can then flow through opening 9 in the cylindrical portion 101a and into the space 11. From the space 11 the drainage fluid may flow out through the outlet 3.

A first tube 27 and a second tube 29 according to at least one possible embodiment are also shown in FIG. 1A. These tubes 27 and 29 connect to the inlet 2 and outlet 3 of the valve, respectively. The first tube 27 connects from the inlet 2 to a body cavity of a patient, such as a brain ventricle, in order to conduct drainage fluid therefrom. The second tube 29 connects from the outlet 3 to another body portion of a patient, such as a cardiovascular or intestinal region, in order to conduct drainage fluid thereto.

FIG. 2A shows a view of a hydrocephalus valve according to at least one possible embodiment of the present application. It should be understood that the embodiment shown in FIG. 2A is one possible embodiment, and other variations and configurations of this embodiment are well within the scope of this application. Some of the reference numerals for corresponding parts or components in other figures have been utilized in this figure. FIG. 2A shows the insertion of a needle 20 through the wall 101b and into the cavity 4. The needle 20 has an opening 20a out of which a liquid, such as a medicament or other liquid, is flowed or dispensed. The flow of the liquid is shown by arrows 25. In the embodiment shown, the force of the liquid flow and/or the increased pressure in the cavity 4 causes the displacement of the plunger 5. The plunger 5 is therefore caused to contact the lever or arm portion 6a connected to the valve cap 6b. The valve cap 6b is consequently lifted or displaced as shown in FIG. 2A, thereby opening the inlet 2 for inflow of the injected liquid. When the plunger 5 is fully displaced as shown in FIG. 2A, the outer ring 5a covers the opening 9, thereby preventing the injected liquid from flowing directly to the outlet and out of the valve. The goal of injecting the liquid is for the liquid to be conveyed or flowed up into the brain ventricles as part of a treatment for hydrocephalus. It is therefore necessary to both hold the valve cap 6b open to allow flow of injected liquid back through the inlet 2, and to close the opening 9 to prevent flow of injected liquid out through the outlet 3. Once the injection process is complete and an amount of liquid is conducted to the brain ventricle, the pressure in the housing drops and the spring 8 causes the plunger 5 to move back to its starting position as shown in FIGS. 1 and 1A. The normal drainage process can resume, and thereby excess injected liquid as well as drainage fluid can flow out of the valve through the outlet.

Figure 2B:
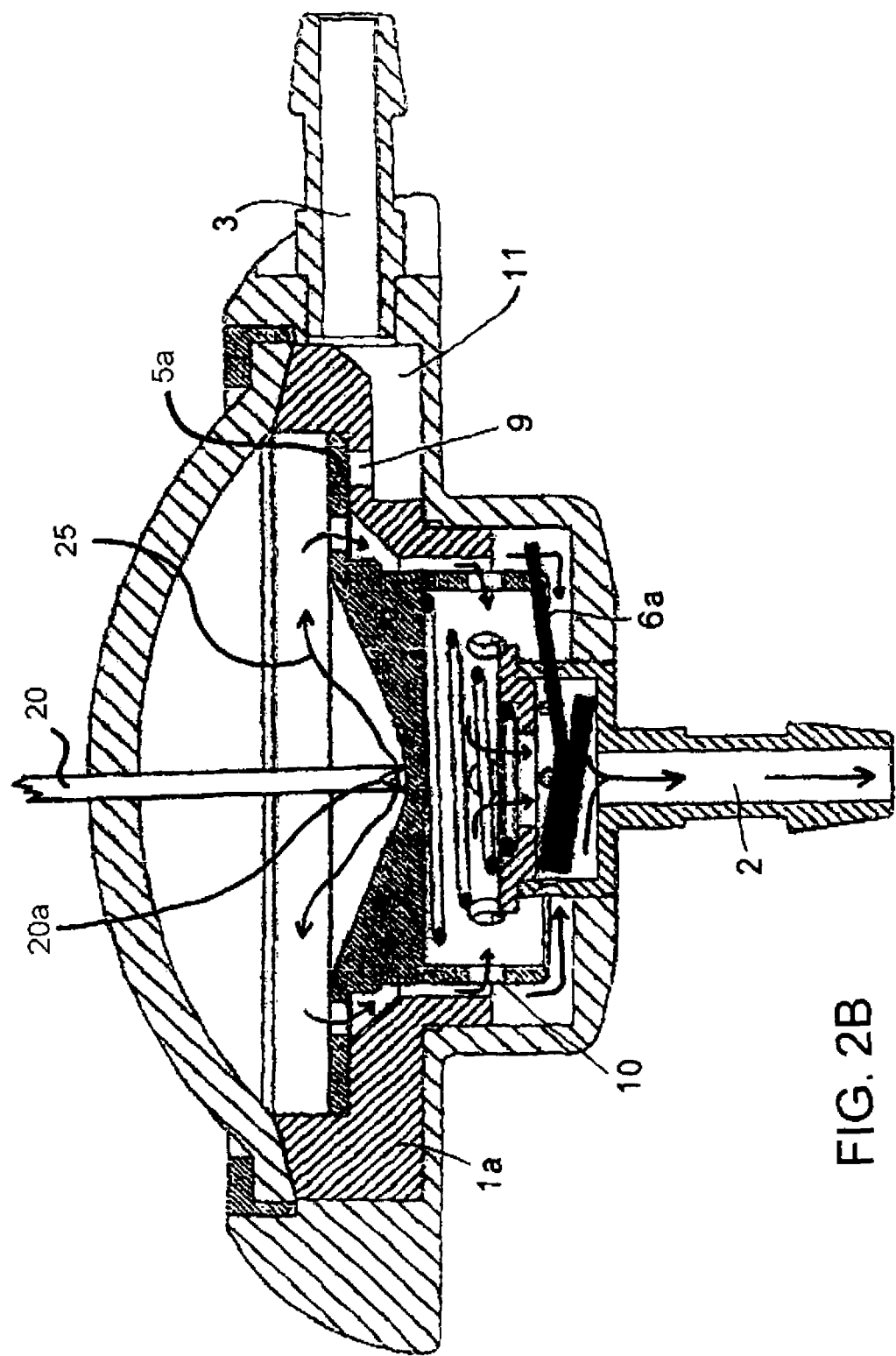
FIG. 2B shows a view of a hydrocephalus valve according to at least one possible embodiment of the present application.
Figure 3:
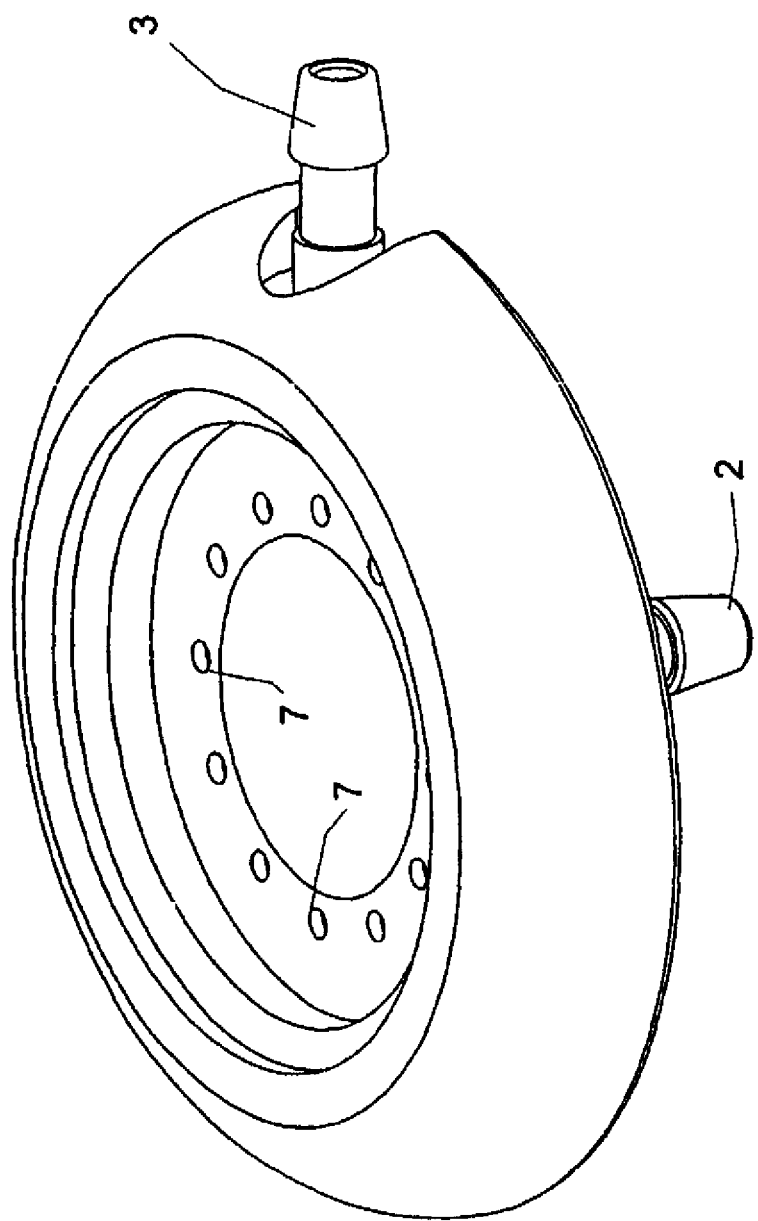
FIG. 3 shows one possible embodiment of an implantable valve in perspective view, in which the valve is illustrated without a wall in order to open up a view into a cavity located underneath adjacent the openings.

FIG. 2B shows a view of a hydrocephalus valve according to at least one possible embodiment of the present application. It should be understood that the embodiment shown in FIG. 2B is one possible embodiment, and other variations and configurations of this embodiment are well within the scope of this application. Some of the reference numerals for corresponding parts or components in other figures have been utilized in this figure. FIG. 2B shows the same injection process as FIG. 2A, except in this embodiment the needle 20 is used to physically contact and move the plunger 5. Because the opening 20a is in the side wall of the needle 20, injected liquid can still flow or be dispensed out of the needle 20 when the tip of the needle 20 is pressed against the plunger 5.

The housing, the inlet and the outlet are in one possible embodiment made of a biocompatible, metallic material or of plastic. In at least one possible embodiment of the present application, the housing, the inlet, and the outlet may comprise titanium.

The diameter of the housing is up to 30 millimeters, in one possible embodiment up to 25 millimeters, for example 21 millimeters, in one possible embodiment up to 20 millimeters, e.g. up to 19 millimeters, in one possible embodiment up to 15 millimeters, with a height of up to 15 millimeters, in one possible embodiment 12 millimeters, in one possible embodiment up to 9 millimeters and in one possible embodiment up to 6 millimeters.

The lever bar in the housing is required and/or desired to match the diameter of the housing, and is therefore smaller. In this regard the free internal diameter of the housing can be wholly or partially filled up. The free internal diameter from the lever bar and the valve cap according to the present application is in one possible embodiment up to 21 millimeters, in another possible embodiment up to 19 millimeters, and in yet another possible embodiment up to 17 millimeters. The height in the housing from the lever bar and the valve cap/valve plate according to the present application is 0.25 millimeter to 4 millimeters, in one possible embodiment 1.8 millimeters.

The spring function can be realized by a spring or a plurality of springs; the diameter can be 0.1 to 0.5 millimeter, in one possible embodiment 0.2 to 0.4 millimeter. The heights can be up to 4.0 millimeters.

A spiral spring with 4 windings is provided in the embodiment. The spiral springs may permit strong compressibility. In other embodiments, springs with 1 to 3 windings are provided.

In the embodiment, the valve cap is circular in shape.

Alternatively, the valve cap/valve plate, the lever bar and the spring can have other shapes, e.g. an elliptical or angular shape.

The internal parts of the valve are in one possible embodiment made of a metallic, biocompatible material. In at least one possible embodiment of the present application, the internal parts of the valve may comprise titanium.

The number and position of the permeable openings 8 and 9 can vary. In this regard, an equal flow volume should be obtained as a function of the width of the openings and the number of openings.

The number of the openings 8 and 9 is 4 to 12 with the diameter between 0.1 and 1 millimeter, in one possible embodiment with 6 to 8 openings with a diameter 0.4 millimeter to 0.8 millimeter.

In the embodiment, the force needed and/or desired to actuate the lever bar is 1 Newton, in other embodiments at least 0.5 Newton, in one possible embodiment at least 1.5 Newton.

The present application comprises a shunt system for drainage and is also suitable for a medicament administration.

Figure 4:
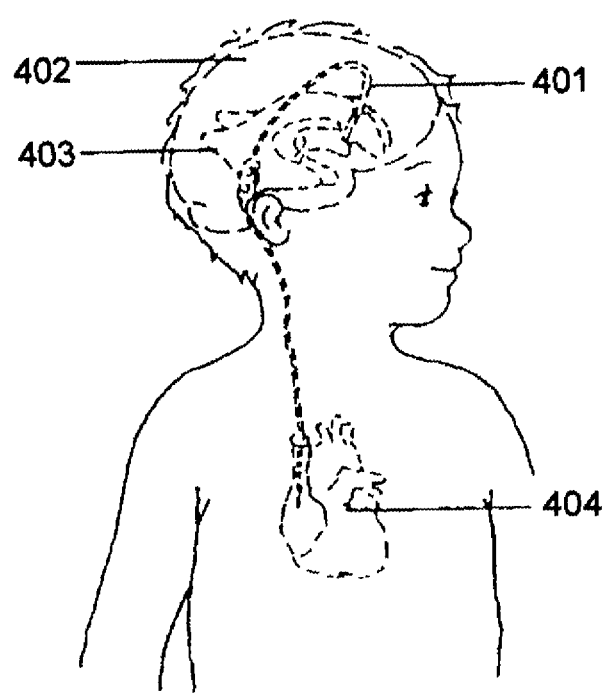
FIG. 4 shows an example of a hydrocephalus treatment device connected to a patient.

FIG. 4 shows an example of a hydrocephalus treatment device connected to a patient. The device comprises a ventriculo-atrial (VA) shunt 401. The VA shunt 401 moves cerebrospinal fluid from the ventricles 403, or spaces in the brain 402, into the atrium, or top chamber, of the heart 404 through a vein in the neck.

Figure 5:
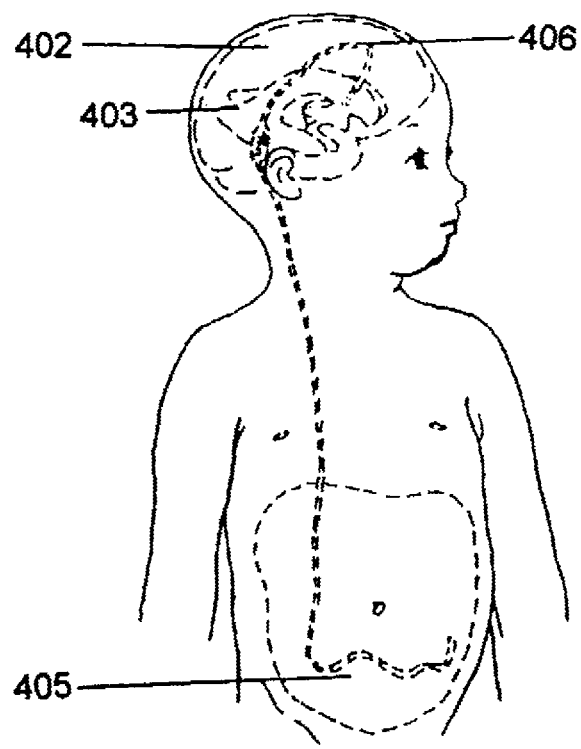
FIG. 5 shows another example of a hydrocephalus treatment device connected to a patient.

FIG. 5 shows an example of a hydrocephalus treatment device connected to a patient. The device comprises a ventriculo-peritoneal (VP) shunt 406. The VP shunt moves cerebrospinal fluid from the ventricles 403, or spaces in the brain 402, to a space in the peritoneal cavity inside the abdominal cavity 405.

One feature or aspect of an embodiment is believed at the time of the filing of this patent application to possibly reside broadly in a subcutaneously implantable shunt with a drainage valve formed as a non-return valve, in one possible embodiment for the drainage of liquor with hydrocephalus, wherein the valve possesses a housing with an inlet and an outlet and wherein the inlet is equipped with a closure that opens on attaining a desired pressure in the drainage liquid, such that the drainage liquid is discharged, in one possible embodiment with a spring that determines the opening pressure for a drainage flow wherein the shunt is equipped with a liquid supply tube or passage for supplying liquid against the drainage direction and that the same tube or passage is intended for the drainage and for the liquid supply, wherein the non-return valve in the drainage tube or passage can be opened for a liquid supply against the drainage direction.

Another feature or aspect of an embodiment is believed at the time of the filing of this patent application to possibly reside broadly in the device, wherein the closure opening is mechanical and/or hydraulic.

Yet another feature or aspect of an embodiment is believed at the time of the filing of this patent application to possibly reside broadly in the device, wherein the closure is opened by a lever.

Still another feature or aspect of an embodiment is believed at the time of the filing of this patent application to possibly reside broadly in the device, wherein the closure actuation is effected by a mechanically and/or hydraulically activatable plunger or by a mechanically and/or hydraulically activatable membrane, wherein the plunger or the membrane remains connected with the lever for the closure opening during the intended supply of liquid against the direction of drainage.

A further feature or aspect of an embodiment is believed at the time of the filing of this patent application to possibly reside broadly in the device, having at least one liquid-containing housing cavity on the side facing away from the closure.

Another feature or aspect of an embodiment is believed at the time of the filing of this patent application to possibly reside broadly in the device, wherein a liquid-containing housing cavity is connected by tubes or passages with the valve inlet and/or with the valve outlet, wherein the closure is provided between the liquid-containing housing cavity and the valve inlet and/or between the valve outlet.

Yet another feature or aspect of an embodiment is believed at the time of the filing of this patent application to possibly reside broadly in the device, wherein at least one housing cavity is provided solely for the drainage liquid.

Still another feature or aspect of an embodiment is believed at the time of the filing of this patent application to possibly reside broadly in the device, wherein at least one housing cavity is provided solely for a liquid that differs from the drainage liquid.

A further feature or aspect of an embodiment is believed at the time of the filing of this patent application to possibly reside broadly in the device, wherein a housing cavity is provided both for drainage liquid as well as for a liquid that differs from the drainage liquid, wherein the housing cavity during the drainage operation is open to the valve inlet and to the valve outlet, wherein the housing cavity during the intended supply of liquid against the direction of drainage is connected to the valve inlet, whereas the valve outlet is closed.

Another feature or aspect of an embodiment is believed at the time of the filing of this patent application to possibly reside broadly in the device, wherein the housing cavity forms a reservoir.

Yet another feature or aspect of an embodiment is believed at the time of the filing of this patent application to possibly reside broadly in the device, wherein the housing, at least in the region of the reservoir, comprises flexible material that is manually deformable.

Still another feature or aspect of an embodiment is believed at the time of the filing of this patent application to possibly reside broadly in the device, wherein the closure actuation is effected by a hydraulically activatable plunger or by a hydraulically activatable membrane, wherein the plunger or the membrane remains connected with the lever for the closure opening during the intended supply of liquid against the direction of drainage, wherein the plunger or the membrane is loaded with liquid partially on both end faces and the resulting plunger pressure or membrane pressure on the plunger surface facing away from the lever or on the membrane surface facing away from the lever is greater than that on the plunger surface facing towards the lever.

A further feature or aspect of an embodiment is believed at the time of the filing of this patent application to possibly reside broadly in the device, wherein the plunger or the membrane is equipped with openings for the passage of a liquid, but the openings are so small that the resulting representative pressure for the liquid flow during the intended liquid flow does not fall below the closing pressure of the closure.

One feature or aspect of an embodiment is believed at the time of the filing of this patent application to possibly reside broadly in the device, comprising a closable opening on the plunger or the membrane.

Another feature or aspect of an embodiment is believed at the time of the filing of this patent application to possibly reside broadly in the device, comprising a syringe for filling the cavity in the housing on the side of the plunger facing away from the lever or on the side of the membrane facing away from the lever.

Yet another feature or aspect of an embodiment is believed at the time of the filing of this patent application to possibly reside broadly in the device, comprising a pierceable housing wall, ine one possible embodiment made of silicone or rubber, on the cavity on the side of the plunger that faces away from the lever or on the side of the membrane that faces away from the lever.

Still another feature or aspect of an embodiment is believed at the time of the filing of this patent application to possibly reside broadly in the device, comprising a syringe content that comprises at least the following volumes
   a) the amount of liquid that is intended to emerge from the drainage tube or passage,
   b) the amount of liquid for filling the drainage tube or passage from the valve up to the outlet end on the drainage tube or passage,
   c) the amount of liquid for filling the cavity in the valve housing through which the liquid flows during the administration of the liquid.

A further feature or aspect of an embodiment is believed at the time of the filing of this patent application to possibly reside broadly in the device, comprising a plunger with at least one guide in the valve housing, in one possible embodiment with a guide at one end and at the other end, wherein at the end facing away from the lever a rim guided in the housing is provided on the plunger.

Another feature or aspect of an embodiment is believed at the time of the filing of this patent application to possibly reside broadly in the device, wherein axially extending openings are provided in the rim of the plunger in order to connect the cavity facing away from the lever in the valve housing and/or a gap is provided between the other end of the plunger facing towards the lever and/or radially extending openings are provided in this plunger end.

Yet another feature or aspect of an embodiment is believed at the time of the filing of this patent application to possibly reside broadly in the device, wherein 4 to 12, in one possible embodiment 6 to 8 radially or axially extending openings are provided.

Still another feature or aspect of an embodiment is believed at the time of the filing of this patent application to possibly reside broadly in the device, wherein the opening width is from 0.1 to 4 millimeters, in one possible embodiment 0.4 to 0.8 millimeter.

A further feature or aspect of an embodiment is believed at the time of the filing of this patent application to possibly reside broadly in the device, wherein the closure is a valve cap or a valve plate or a ball.

Another feature or aspect of an embodiment is believed at the time of the filing of this patent application to possibly reside broadly in the device, wherein a valve cap or a valve plate is guided in an unarticulated manner in the valve housing.

Yet another feature or aspect of an embodiment is believed at the time of the filing of this patent application to possibly reside broadly in the device, wherein a spring that determines the opening pressure is provided on the closure, wherein, in the closed position of the valve cap or valve plate or ball, the spring is located at a distance.

Still another feature or aspect of an embodiment is believed at the time of the filing of this patent application to possibly reside broadly in the device, wherein the spring in the closed position of the valve cap or valve plate lies against the valve cap or the valve plate in a pressureless manner.

A further feature or aspect of an embodiment is believed at the time of the filing of this patent application to possibly reside broadly in the device, wherein the spring in the closed position of the valve cap or valve plate presses against the valve cap or the valve plate.

One feature or aspect of an embodiment is believed at the time of the filing of this patent application to possibly reside broadly in the device, wherein, by moving under compression of the spring, the valve cap or the valve plate uncovers at least one discharge opening for drainage liquid.

Another feature or aspect of an embodiment is believed at the time of the filing of this patent application to possibly reside broadly in the device, wherein the plunger or membrane possesses a plurality of discharge openings that are uniformly distributed on the periphery.

Yet another feature or aspect of an embodiment is believed at the time of the filing of this patent application to possibly reside broadly in the device, wherein the spring, on the end that faces away from the closure, is supported on the membrane or plunger.

Still another feature or aspect of an embodiment is believed at the time of the filing of this patent application to possibly reside broadly in the device, comprising a spiral spring, whose spring coils are spaced apart from one another in the axial direction.

A further feature or aspect of an embodiment is believed at the time of the filing of this patent application to possibly reside broadly in the device, wherein the spiral spring exhibits 1 to 4 spring coils and/or a spring wire diameter of 0.1 to 0.5 millimeter, in one possible embodiment 0.2 to 0.4 millimeter and/or a diameter on the closure side of 1.5 to 3 millimeters, in one possible embodiment 2 to 3 millimeters and/or a diameter on the plunger side of 4 to 10 millimeters, in one possible embodiment 5.5 to 7.5 millimeters and/or an extension of the spring of up to 4 millimeters in the axial direction.

Another feature or aspect of an embodiment is believed at the time of the filing of this patent application to possibly reside broadly in the device, wherein the lever on the closure is an angle lever, of which one end is connected rigidly with the valve cap or the valve plate and the other end of which projects into the movement path of the plunger.

Yet another feature or aspect of an embodiment is believed at the time of the filing of this patent application to possibly reside broadly in the device, wherein the lever end that faces away from the closure is subjected to a pressure of at least 0.5 Newton, in one possible embodiment at least 1.5 Newton.

Still another feature or aspect of an embodiment is believed at the time of the filing of this patent application to possibly reside broadly in the device, wherein the plunger closes the outlet of the valve during the supply of liquid.

A further feature or aspect of an embodiment is believed at the time of the filing of this patent application to possibly reside broadly in the device, wherein the plunger closes the outlet of the valve with its rim during the supply of liquid.

Another feature or aspect of an embodiment is believed at the time of the filing of this patent application to possibly reside broadly in the device, wherein the plunger is equipped with a funnel shaped surface on the side facing away from the lever.

Yet another feature or aspect of an embodiment is believed at the time of the filing of this patent application to possibly reside broadly in the device, wherein the side of the plunger that faces away from the lever is designed to be non-slip or has a non-slip coating.

Still another feature or aspect of an embodiment is believed at the time of the filing of this patent application to possibly reside broadly in the device, wherein the external diameter of the valve is maximum 30 millimeters, in one possible embodiment maximum 20 millimeters, in another possible embodiment maximum 15 millimeters and/or the thickness/height of the valve is up to 15 millimeters, in another possible embodiment up to 12 millimeters, in another possible embodiment up to 9 millimeters and in another possible embodiment up to 6 millimeters.

A further feature or aspect of an embodiment is believed at the time of the filing of this patent application to possibly reside broadly in the device, wherein the valve cap or the valve plate is tiltable at an angle.

Another feature or aspect of an embodiment is believed at the time of the filing of this patent application to possibly reside broadly in the device possessing a straight tilt angle.

Yet another feature or aspect of an embodiment is believed at the time of the filing of this patent application to possibly reside broadly in the device possessing a rectangular valve cap or a rectangular valve plate.

Still another feature or aspect of an embodiment is believed at the time of the filing of this patent application to possibly reside broadly in the device, wherein the valve comprises completely or partly a biocompatible material, in one possible embodiment at least partly of metal or plastic or at least partly of both.

A further feature or aspect of an embodiment is believed at the time of the filing of this patent application to possibly reside broadly in the device, wherein titanium is used as the metal.

The components disclosed in the various publications, disclosed or incorporated by reference herein, may possibly be used in possible embodiments of the present invention, as well as equivalents thereof.

The purpose of the statements about the technical field is generally to enable the Patent and Trademark Office and the public to determine quickly, from a cursory inspection, the nature of this patent application. The description of the technical field is believed, at the time of the filing of this patent application, to adequately describe the technical field of this patent application. However, the description of the technical field may not be completely applicable to the claims as originally filed in this patent application, as amended during prosecution of this patent application, and as ultimately allowed in any patent issuing from this patent application. Therefore, any statements made relating to the technical field are not intended to limit the claims in any manner and should not be interpreted as limiting the claims in any manner.

The appended drawings in their entirety, including all dimensions, proportions and/or shapes in at least one embodiment of the invention, are accurate and are hereby included by reference into this specification.

The background information is believed, at the time of the filing of this patent application, to adequately provide background information for this patent application. However, the background information may not be completely applicable to the claims as originally filed in this patent application, as amended during prosecution of this patent application, and as ultimately allowed in any patent issuing from this patent application. Therefore, any statements made relating to the background information are not intended to limit the claims in any manner and should not be interpreted as limiting the claims in any manner.

All, or substantially all, of the components and methods of the various embodiments may be used with at least one embodiment or all of the embodiments, if more than one embodiment is described herein.

The purpose of the statements about the object or objects is generally to enable the Patent and Trademark Office and the public to determine quickly, from a cursory inspection, the nature of this patent application. The description of the object or objects is believed, at the time of the filing of this patent application, to adequately describe the object or objects of this patent application. However, the description of the object or objects may not be completely applicable to the claims as originally filed in this patent application, as amended during prosecution of this patent application, and as ultimately allowed in any patent issuing from this patent application. Therefore, any statements made relating to the object or objects are not intended to limit the claims in any manner and should not be interpreted as limiting the claims in any manner.

All of the patents, patent applications and publications recited herein, and in the Declaration attached hereto, are hereby incorporated by reference as if set forth in their entirety herein except for the exceptions indicated herein.

The summary is believed, at the time of the filing of this patent application, to adequately summarize this patent application. However, portions or all of the information contained in the summary may not be completely applicable to the claims as originally filed in this patent application, as amended during prosecution of this patent application, and as ultimately allowed in any patent issuing from this patent application. Therefore, any statements made relating to the summary are not intended to limit the claims in any manner and should not be interpreted as limiting the claims in any manner.

It will be understood that the examples of patents, published patent applications, and other documents which are included in this application and which are referred to in paragraphs which state "Some examples of . . . which may possibly be used in at least one possible embodiment of the present application . . . " may possibly not be used or useable in any one or more embodiments of the application.

The sentence immediately above relates to patents, published patent applications and other documents either incorporated by reference or not incorporated by reference.

Some examples of valves which may possibly be utilized or adapted for use in at least one possible embodiment according to the present application may possibly be found in the following patents: DE 69832445 T2, DE 69725762 T2, DE 69707333 T2, DE 69703744 T2, DE 69325384 T2, DE 69313260 T2, DE 69001549 T2, DE 102007059300, U.S. Pat. No. 7,025,739, U.S. Pat. No. 6,875,192, U.S. Pat. No. 6,575,928, U.S. Pat. No. 6,383,159, U.S. Pat. No. 6,083,179, U.S. Pat. No. 5,795,307, and U.S. Pat. No. 5,368,556.

Some examples of chambers which may possibly be utilized or adapted for use in at least one possible embodiment according to the present application may possibly be found in the following patents: DE 69725762 T2, EP 2055227 A1, U.S. Pat. No. 5,728,061, U.S. Pat. No. 5,928,182, U.S. Pat. No. 5,637,083, U.S. Pat. No. 5,167,615, U.S. Pat. No. 5,154,693, U.S. Pat. No. 4,560,375, U.S. Pat. No. 3,769,982, U.S. Pat. No. 3,768,508, and US 2002/0026139 A1.

Some examples of walls which may possibly be utilized or adapted for use in at least one possible embodiment according to the present application may possibly be found in the following patents: DE 60318761, DE 602004013072, DE 19557921, EP 0819012/1996090910349, and EP 0646381.

U.S. Pat. No. 7,766,855, having patent application Ser. No. 11/535,242, filed on Sep. 26, 2006, having inventor Christoph Miethke, and title "ADJUSTABLE HYDROCEPHALUS VALVE," and its corresponding Federal Republic of Germany Patent Application No. 10 2004 015 500, filed on Mar. 27, 2004, and International Patent Application No. PCT/EP2005/003052, filed on Mar. 22, 2005, having WIPO Publication No. WO2005092424 and inventor Christoph Miethke are hereby incorporated by reference as if set forth in their entirety herein.

U.S. Pat. No. 7,422,566, having patent application Ser. No. 11/149,928, filed on Jun. 10, 2005, having inventor Christoph MIETHKE, and title "METHOD OF TREATING A PATIENT WITH HYDROCEPHALUS AND APPARATUS THEREFOR," and its corresponding Federal Republic of Germany Patent Application No. 103 47 278.9, filed on Oct. 8, 2003, and Federal Republic of Germany Patent Application No. 102 58 070.7, filed on Dec. 11, 2002, and International Patent Application No. PCT/EP03/13999, filed on Dec. 10, 2003, having WIPO Publication No. WO2005092424 and inventor Christoph MIETHKE are hereby incorporated by reference as if set forth in their entirety herein.

The patents, patent applications, and patent publications listed above in the preceding paragraphs are herein incorporated by reference as if set forth in their entirety except for the exceptions indicated herein. The purpose of incorporating U.S. patents, Foreign patents, publications, etc. is solely to provide additional information relating to technical features of one or more embodiments, which information may not be completely disclosed in the wording in the pages of this application. However, words relating to the opinions and judgments of the author and not directly relating to the technical details of the description of the embodiments therein are not incorporated by reference. The words all, always, absolutely, consistently, preferably, guarantee, particularly, constantly, ensure, necessarily, immediately, endlessly, avoid, exactly, continually, expediently, ideal, need, must, only, perpetual, precise, perfect, require, requisite, simultaneous, total, unavoidable, and unnecessary, or words substantially equivalent to the above-mentioned words in this sentence, when not used to describe technical features of one or more embodiments of the patents, patent applications, and patent publications, are not considered to be incorporated by reference herein.

The corresponding foreign and international patent publication applications, namely, Federal Republic of Germany Patent Application No. 10 2009 060 533.9, filed on Dec. 23, 2009, having inventor Christoph MIETHKE, and DE-OS 10 2009 060 533.9 and DE-PS 10 2009 060 533.9, and International Application No. PCT/EP2010/007817, filed on Dec. 21, 2010, having WIPO Publication No. WO 2011/076382 and inventor Christoph MIETHKE, are hereby incorporated by reference as if set forth in their entirety herein, except for the exceptions indicated herein, for the purpose of correcting and explaining any possible misinterpretations of the English translation thereof. In addition, the published equivalents of the above corresponding foreign and international patent publication applications, and other equivalents or corresponding applications, if any, in corresponding cases in the Federal Republic of Germany and elsewhere, and the references and documents cited in any of the documents cited herein, such as the patents, patent applications and publications, except for the exceptions indicated herein, are hereby incorporated by reference as if set forth in their entirety herein except for the exceptions indicated herein.

The purpose of incorporating the corresponding foreign equivalent patent application(s), that is, PCT/EP2010/007817 and German Patent Application 10 2009 060 533.9, is solely for the purpose of providing a basis of correction of any wording in the pages of the present application, which may have been mistranslated or misinterpreted by the translator. However, words relating to opinions and judgments of the author and not directly relating to the technical details of the description of the embodiments therein are not to be incorporated by reference. The words all, always, absolutely, consistently, preferably, guarantee, particularly, constantly, ensure, necessarily, immediately, endlessly, avoid, exactly, continually, expediently, ideal, need, must, only, perpetual, precise, perfect, require, requisite, simultaneous, total, unavoidable, and unnecessary, or words substantially equivalent to the above-mentioned word in this sentence, when not used to describe technical features of one or more embodiments of the patents, patent applications, and patent publications, are not generally considered to be incorporated by reference herein.

Statements made in the original foreign patent applications PCT/EP2010/007817 and DE 10 2009 060 533.9 from which this patent application claims priority which do not have to do with the correction of the translation in this patent application are not to be included in this patent application in the incorporation by reference.

Any statements about admissions of prior art in the original foreign patent applications PCT/EP2010/007817 and DE 10 2009 060 533.9 are not to be included in this patent application in the incorporation by reference, since the laws relating to prior art in non-U.S. Patent Offices and courts may be substantially different from the Patent Laws of the United States.

All of the references and documents cited in any of the documents cited herein, except for the exceptions indicated herein, are hereby incorporated by reference as if set forth in their entirety herein except for the exceptions indicated herein. All of the documents cited herein, referred to in the immediately preceding sentence, include all of the patents, patent applications and publications cited anywhere in the present application.

The description of the embodiment or embodiments is believed, at the time of the filing of this patent application, to adequately describe the embodiment or embodiments of this patent application. However, portions of the description of the embodiment or embodiments may not be completely applicable to the claims as originally filed in this patent application, as amended during prosecution of this patent application, and as ultimately allowed in any patent issuing from this patent application. Therefore, any statements made relating to the embodiment or embodiments are not intended to limit the claims in any manner and should not be interpreted as limiting the claims in any manner.

The details in the patents, patent applications and publications may be considered to be incorporable, at applicant's option, into the claims during prosecution as further limitations in the claims to patentably distinguish any amended claims from any applied prior art.

The purpose of the title of this patent application is generally to enable the Patent and Trademark Office and the public to determine quickly, from a cursory inspection, the nature of this patent application. The title is believed, at the time of the filing of this patent application, to adequately reflect the general nature of this patent application. However, the title may not be completely applicable to the technical field, the object or objects, the summary, the description of the embodiment or embodiments, and the claims as originally filed in this patent application, as amended during prosecution of this patent application, and as ultimately allowed in any patent issuing from this patent application. Therefore, the title is not intended to limit the claims in any manner and should not be interpreted as limiting the claims in any manner.

The abstract of the disclosure is submitted herewith as required by 37 C.F.R. §1.72(b). As stated in 37 C.F.R. §1.72(b):

A brief abstract of the technical disclosure in the specification must commence on a separate sheet, preferably following the claims, under the heading "Abstract of the Disclosure." The purpose of the abstract is to enable the Patent and Trademark Office and the public generally to determine quickly from a cursory inspection the nature and gist of the technical disclosure. The abstract shall not be used for interpreting the scope of the claims.

Therefore, any statements made relating to the abstract are not intended to limit the claims in any manner and should not be interpreted as limiting the claims in any manner.

The embodiments of the invention described herein above in the context of the preferred embodiments are not to be taken as limiting the embodiments of the invention to all of the provided details thereof, since modifications and variations thereof may be made without departing from the spirit and scope of the embodiments of the invention.

What is claimed is:

1. A hydrocephalus shunt drainage valve configured to be installed in a subcutaneously implantable shunt for draining cerebrospinal fluid from the brain of a patient with hydrocephalus, said valve comprising:
   a housing being configured to house cerebrospinal fluid;
   said housing comprising an inlet being configured to be operatively connected to the brain of a patient with hydrocephalus to permit drainage of cerebrospinal fluid from the brain of the patient into said housing;
   said housing comprising an outlet being configured to permit drainage of cerebrospinal fluid that was drained from the brain of the patient out of said housing;
   a valve arrangement disposed in said housing and configured to control flow of liquid through in said housing;
   said valve arrangement comprising a non-return closure and a displaceable element;
   said non-return closure comprising an inlet side and an outlet side;
   said non-return closure being configured to open upon liquid pressure on said inlet side being at or above liquid pressure on said outlet side, to thereby permit cerebrospinal fluid being drained from the brain of the patient to flow into said housing via said inlet;
   said non-return closure being configured to close upon liquid pressure on said inlet side being below liquid pressure on said outlet side, to thereby prevent drained cerebrospinal fluid from flowing back to the brain of the patient via said inlet; and
   said displaceable element being configured to be displaced upon exertion of a force on said displaceable element during supply of a medicament liquid into said housing, to thereby:
      engage and open said non-return closure to permit delivery of the medicament liquid in said housing to the brain of the patient via said inlet against the direction of flow of cerebrospinal fluid, and
      substantially simultaneously close said outlet to block unwanted drainage of the medicament liquid out of said housing via said outlet.

2. The hydrocephalus shunt drainage valve according to claim 1, wherein said displaceable element is configured to be displaced by a mechanical force and/or a hydraulic force, and is configured to remain in engagement with said closure to keep said closure open during delivery of the medicament liquid in said housing to the brain of the patient via said inlet against the direction of flow of cerebrospinal fluid.

3. The hydrocephalus shunt drainage valve according to claim 2, wherein:
said displaceable element comprises a first end face that faces substantially toward said closure, and a second end face that faces substantially away from said closure; and
said displaceable element is configured such that, during delivery of the medicament liquid into said housing, the liquid pressure on said second end face is sufficient to at least assist in the displacement of said displaceable element.

4. The hydrocephalus shunt drainage valve according to claim 3, wherein said displaceable element comprises a plunger or a membrane.

5. The hydrocephalus shunt drainage valve according to claim 4, wherein:
said displaceable element comprises openings therein configured to permit the passage of liquid through said displaceable element; and
said openings are of a size configured to restrict flow therethrough to thereby generate the liquid pressure on said second end face that is sufficient to at least assist in the displacement of said displaceable element during delivery of the medicament liquid into said housing.

6. The hydrocephalus shunt drainage valve according to claim 5, wherein:
the interior of said housing is divided by said valve arrangement into a plurality of housing cavities configured to receive and house liquid therein;
each of said housing cavities is operatively connected by passages to at least one of: another housing cavity, said housing inlet, and said housing outlet; and
at least one of (A), (B), and (C):
at least one of said housing cavities is configured to solely house cerebrospinal fluid;
at least one of said housing cavities is configured to solely house a liquid other than cerebrospinal fluid; and
at least one of said housing cavities is configured to house both cerebrospinal fluid and a liquid other than cerebrospinal fluid.

7. The hydrocephalus shunt drainage valve according to claim 6, wherein:
one of said housing cavities comprises a reservoir disposed on a side of said housing;
said displaceable element is disposed between said closure and said reservoir;
said second end face of said displaceable element is disposed to face substantially toward said reservoir;
said housing comprises a reservoir wall portion that comprises a flexible material that is manually deformable; and
said flexible material comprises a pierceable silicone or rubber material configured to permit delivery of the medicament liquid into said reservoir through said reservoir wall portion.

8. The hydrocephalus shunt drainage valve according to claim 7, wherein:
said displaceable element comprises solely a plunger; and
said valve arrangement comprises a guide configured to guide said plunger upon displacement of said plunger.

9. The hydrocephalus shunt drainage valve according to claim 8, wherein:
said plunger comprises a substantially hollow body portion and a rim portion that is disposed adjacent said second end face and projects away from said body portion; and
at least one of (D), (E), and (F):
(D) said rim portion comprises openings to permit flow of liquid through said rim portion to and from said reservoir;
(E) said body portion comprises openings to permit flow of liquid through said body portion to and from adjacent housing cavities; and
(F) said body portion has an outer diameter smaller than an inner diameter of said guide such that a gap is provided therebetween to permit the flow of liquid around said body portion.

10. The hydrocephalus shunt drainage valve according to claim 9, wherein:
said plunger closes said housing outlet with said rim during delivery of said medicament liquid;
said closure comprises a valve cap, a valve plate, a rectangular valve cap, or a rectangular valve plate configured to cover the opening in said housing inlet; and
said valve arrangement comprises a closure housing which substantially surrounds said closure.

11. The hydrocephalus shunt drainage valve according to claim 10, wherein:
said valve arrangement comprises a spring disposed between said closure housing and said plunger and configured to hold said plunger in a stationary position;
said plunger is configured, upon displacement of said plunger during delivery of the medicament liquid into said reservoir, to compress said spring against said closure housing;
said spring is configured to return said plunger to its stationary position upon completion of displacement of said plunger and completion of delivery of the medicament liquid to the brain of a patient.

12. The hydrocephalus shunt drainage valve according to claim 11, wherein said second end face of said plunger comprises a funnel-shaped surface that is configured to guide and center an end portion of syringe pressed against said second end face, and is configured to be non-slip or has a non-slip coating.

13. The hydrocephalus shunt drainage valve according to claim 12, wherein:
said spring is configured to be overcome by a pressing force of at least 0.5 newtons or 1.5 newtons to permit engagement and opening of said closure with said plunger;
said closure consists of titanium or other biocompatible metal, biocompatible plastic, or a combination thereof;
said spring is a spiral spring that exhibits 1 to 4 spring coils and/or a spring wire diameter of 0.1 to 0.5 millimeter or 0.2 to 0.4 millimeter, and/or a diameter on the closure side of 1.5 to 3 millimeters or 2 to 3 millimeters, and/or a diameter on the plunger side of 4 to 10 millimeters or 5.5 to 7.5 millimeters, and/or an extension of the spring of up to 4 millimeters in the axial direction;
said plunger comprises 6 to 8 of said radially or axially extending openings;
the width of said openings is from 0.1 to 4 millimeters or from 0.4 to 0.8 millimeter; and
the external diameter of said valve is a maximum of 15, 20, or 30, and/or the thickness/height of said valve is up to 6, 9, 12, or 15.

14. The hydrocephalus shunt drainage valve according to claim 2, wherein:
said closure comprises a cap or plate and a lever connected thereto; and said displaceable element is configured to engage said lever to displace said cap or plate and thereby open said closure.

15. The hydrocephalus shunt drainage valve according to claim 14, wherein:
   said lever is oriented at an angle with respect to said cap or plate; and
   said displaceable element is configured to engage said lever to tilt said cap or plate at an angle.

16. A method of using a hydrocephalus shunt drainage valve installed in a subcutaneously implantable shunt for draining cerebrospinal fluid from the brain of a patient with hydrocephalus, said valve comprising:
   a housing being configured to house cerebrospinal fluid;
   said housing comprising an inlet being operatively connected to the brain of a patient with hydrocephalus to permit drainage of cerebrospinal fluid from the brain of the patient into said housing;
   said housing comprising an outlet being configured to permit drainage of cerebrospinal fluid that was drained from the brain of the patient out of said housing;
   a valve arrangement disposed in said housing and configured to control flow of liquid through in said housing;
   said valve arrangement comprising a non-return closure and a displaceable element;
   said non-return closure comprising an inlet side and an outlet side;
   said non-return closure being configured to open upon liquid pressure on said inlet side being at or above liquid pressure on said outlet side, to thereby permit cerebrospinal fluid being drained from the brain of the patient to flow into said housing via said inlet;
   said non-return closure being configured to close upon liquid pressure on said inlet side being below liquid pressure on said outlet side, to thereby prevent drained cerebrospinal fluid from flowing back to the brain of the patient via said inlet; and
   said displaceable element being configured to be displaced upon exertion of a force on said displaceable element during supply of a medicament liquid into said housing, to thereby:
      engage and open said non-return closure to permit delivery of the medicament liquid in said housing to the brain of the patient via said inlet against the direction of flow of cerebrospinal fluid, and
      substantially simultaneously close said outlet to block unwanted drainage of the medicament liquid out of said housing via said outlet, and
   said method comprising the steps of:
      delivering the medicament liquid into said housing and substantially simultaneously exerting a force and displacing said displaceable element; and
      engaging and opening said non-return closure with said displaceable element, and delivering the medicament liquid in said housing to the brain of the patient via said inlet against the direction of flow of cerebrospinal fluid, and substantially simultaneously closing said outlet and thereby blocking unwanted drainage of the medicament liquid out of said housing via said outlet.

17. The method according to claim 16, wherein said step of exerting a force comprises exerting a mechanical and/or hydraulic force.

18. The method according to claim 17, wherein:
   said displaceable element comprises a plunger;
   said step of delivering the medicament liquid comprises inserting a syringe through a flexible wall portion of said housing and into a reservoir in said housing adjacent said plunger;
   said step of displacing said plunger comprises at least one of (A) and (B):
      (A) dispensing medicament liquid into said reservoir and thereby increasing liquid pressure in said reservoir; and
      displacing said plunger via hydraulic force generated by said increased liquid pressure; and
      (B) contacting said plunger with an end portion of said syringe; and
      displacing said plunger via mechanical force generated by pressing said plunger with said syringe.

19. The method according to claim 18, wherein said syringe contains one of the following volumes (D), (E), and (F):
   (D) the amount of medicament liquid that is intended to emerge from the drainage tube or passage,
   (E) the amount of medicament liquid for filling the drainage tube or passage from the valve up to the outlet end on the drainage tube or passage,
   (F) the amount of medicament liquid for filling the cavity in the valve housing through which the medicament liquid flows during the delivery of the medicament liquid.

20. The method according to claim 16, wherein said closure comprises a cap or plate and a lever connected thereto, and said step of engaging and opening said closure with said displaceable element comprises engaging said lever with said displaceable element and displacing said cap or plate.

* * * * *